United States Patent [19]

Masumura et al.

[11] Patent Number: 4,942,171
[45] Date of Patent: Jul. 17, 1990

[54] THE COMPOUND, 6-(1-IMIDAZOLYL METHYL)-5,6,7,8-TETRAHYDRONAPHTHALENE-2-CARBOXYLIC ACID AND SALTS THEREOF HAVING ANTIDIABETIC ACTIVITY

[75] Inventors: Hidemi Masumura; Kyoko Sakuma; Shinichiro Ashida, all of Tokyo, Japan

[73] Assignee: Daiichi Seiyaku Co., Ltd., Tokyo, Japan

[21] Appl. No.: 215,488

[22] Filed: Jul. 6, 1988

[30] Foreign Application Priority Data

Jul. 7, 1987 [JP] Japan .................................. 62-169486

[51] Int. Cl.$^5$ .................. C07D 233/60; A61K 31/415
[52] U.S. Cl. ..................................... 514/399; 514/277; 514/365; 546/341; 546/342; 548/204; 548/344
[58] Field of Search ................ 546/342, 341; 548/341, 548/204; 514/277, 365, 399

[56] References Cited

U.S. PATENT DOCUMENTS 4,665,188  5/1987  Kanao .................. 548/341
4,766,127  8/1988  Martinez et al. ..... 514/277

Primary Examiner—Alan L. Rotman
Attorney, Agent, or Firm—Sughrue, Mion, Zinn, MacPeak & Seas

[57] ABSTRACT

An antidiabetic agent is disclosed, which comprises a compound represented by formula (I):

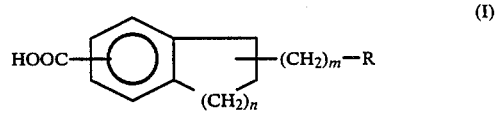

wherein R represents an imidazolyl group, a thiazolyl group or a pyridyl group; n represents 1 or 2; and m represents an integer of from 1 to 4, or a pharmaceutically acceptable salt thereof as an active ingredient.

2 Claims, No Drawings

THE COMPOUND, 6-(1-IMIDAZOLYL METHYL)-5,6,7,8-TETRAHYDRONAPHTHALENE-2-CARBOXYLIC ACID AND SALTS THEREOF HAVING ANTIDIABETIC ACTIVITY

FIELD OF THE INVENTION

This invention relates to an antidiabetic agent which comprises a compound represented by formula (I):

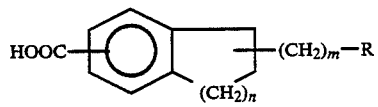

wherein R represents an imidazolyl group, a thiazolyl group or a pyridyl group; n represents 1 or 2; and m represents an integer of from 1 to 4, or a pharmaceutically acceptable salt thereof as an active ingredient.

BACKGROUND OF THE INVENTION

The compounds of formula (I) are known to inhibit the synthesis of thromboxane $A_2$ and have therapeutic effects on ischemic heart diseases (U.S. Pat. No. 4,665,188), but are unknown for their antidiabetic effects.

(E)-3-(4-(1-Imidazolylmethyl)phenyl)propenoic acid hydrochloride is known to inhibit the synthesis of thromboxane $A_2$. This compound was orally administered to diabetic test animals, however, the effect obtained was not satisfactory for the treatment (Abstract of the 27th Congress of the Japanese Society of Nephrology 196, (1984)).

SUMMARY OF THE INVENTION

The inventors have conducted extensive research to find compounds having antidiabetic effects. As a result, it has now been found that the compounds represented by formula (I) exhibit the above-described effects, thus reaching the present invention.

This invention relates to an antidiabetic agent which comprises a compound represented by formula (I) or a pharmaceutically acceptable salt thereof as an active ingredient.

DETAILED DESCRIPTION OF THE INVENTION

Pharmaceutically acceptable salts of the compounds of formula (I) include acid addition salts formed with inorganic acids, e.g., hydrochloric acid, sulfuric acid, nitric acid, etc., or organic acids, e.g., fumaric acid, tartaric acid, maleic acid, succinic acid, oxalic acid, etc., and salts formed from a carboxyl group and an alkali metal, e.g., sodium, potassium, etc., or an alkaline earth metal, e.g., calcium, magnesium, etc.

The compounds of formula (I) and salts thereof proved highly safe on examination of acute toxicity ($LD_{50}$) in oral administration or intravenous injection to rats.

The compounds of formula (I) or a salt thereof can be formulated into various pharmaceutical preparations, such as tablets, powders, capsules, and injectable solutions, according to known pharmaceutical techniques and is usually administered orally or intravenously.

The dose level of the compounds of formula (I) or a salt thereof generally ranges from 50 to 1000 mg/day for an adult (body weight: about 50 to 60 kg) in oral administration.

The compounds of formula (I) or a salt thereof experimentally exhibited excellent antidiabetic effects such as hypoglycemic activity and improvement of glucose tolerance in a diabetic model such as streptozotocin-induced diabetic spontaneous hypertensive rats, and also exhibited no significant side effects in case of long term oral administration. Therefore, the compounds of formula (I) or a salt thereof are useful as an diabetic agent.

The present invention is now illustrated in greater detail with reference to the following Test Example and Reference Example, but it should be understood that the present invention is not limited thereto.

TEST EXAMPLE 1

Efficacy in Diabetic Model

Test Animal:

5-Week old spontaneous hypertensive male rats (SHR), available from Nippon Charles River, were used. Streptozotocin (STZ) was dissolved in a 0.1M citrate buffer solution (pH 4.5) and injected into the tail vein of the rats at a dose level of 50 mg/kg to prepare diabetic rats. For control, rats received 1 ml/kg of the citrate buffer solution alone through administration to the tail vein. After one week from the STZ administration, blood was taken from the tail vein of the unanesthetized rats, and the blood sugar level was determined. Those rats having a blood sugar level of 300 mg/dl or higher were used as diabetic rats.

Administration of Drug:

6-(1-Imidazolylmethyl)-5,6,7,8-tetrahydronaphthalene- 2-carboxylic acid hydrochloride hemihydrate (hereinafter referred to as Compound A) was dissolved in distilled water and administered orally to the test animals at a dose level of 1 mg/kg/day or 10 mg/kg/day for 5 consecutive months from one week after the administration of STZ or a citrate buffer solution.

Determination of Blood Sugar Level

Just before the administration of Compound A, blood was sampled from the tail vein of the rats without any restriction of diet to determine the blood sugar level using a commercial glucose assay kit (Trade name: New Blood Sugar Test, produced by Boehringer Mannheim Co., Ltd., West Germany). The results are shown in Table 1, expressed as mean ±S.E.

Determination of Glucose Tolerance

After 3 months from the start of the administration of Compound A, the rats were fasted for 18 hours. Glucose was administered orally to the rats at a dose level of 2 g/kg. Blood was sampled from the tail vein of the rats just before the administration of glucose and at 1 hour and 2 hours after the administration to determine the blood sugar lever using the above method. The result was shown in Table 2, expressed as mean +S.E.

Result

TABLE 1

| | Hypoglycemic Activity | | |
|---|---|---|---|
| Administration Term (weeks) | Blood Sugar Level (mg/dl) Dosage of Compound A (mg/kg/day) | | |
| | 0 | 1 | 10 |
| SHR (n = 8) | 0   103.8 ± 2.5 | 100.7 ± 1.6 | 108.0 ± 3.2 |
| | 2   96.6 ± | 95.4 ± | 90.9 ± |

TABLE 1-continued

| | Hypoglycemic Activity | | | |
|---|---|---|---|---|
| | Administration Term (weeks) | Blood Sugar Level (mg/dl) Dosage of Compound A (mg/kg/day) | | |
| | | 0 | 1 | 10 |
| | 8 | 94.2 ± 1.5 | 94.5 ± 1.5 | 93.2 ± 1.8 |
| Diabetic SHR (n = 7) | 0 | 356.1 ± 9.6 | 374.6 ± 17.3 | 361.4 ± 10.6 |
| | 2 | 481.5 ± 36.4 | 406.3 ± 39.9 | 365.2 ± 40.9* |
| | 8 | 544.2 ± 30.0 | 445.0 ± 57.6 | 277.3 ± 44.7** | n: Number of test animals
*P < 0.05 compared with the control group (not administered Compound A)
**P < 0.01 Compared with the control group As is apparent from Table 1, Compound A exhibited a tendency to lower the high blood sugar level of the diabetic SHR from 2 weeks after the start of the administration of Compound A, and significantly lowered the blood sugar level at 8 weeks after the start of the administration of Compound A. However, the blood sugar level in SHR was not affected by the administration of Compound A. Therefore, it was confirmed that Compound A lowered the high blood sugar level in diabetic animals.

TABLE 2

| | Effect on Glucose Tolerance | | |
|---|---|---|---|
| | Blood Sugar Level (mg/dl) Dosage of Compound A (mg/kg/day) | | |
| Sampling Time | 0 (n = 7) | 1 (n = 7) | 10 (n = 8) |
| Just Before the Glucose load | 178.5 ± 32.8 | 136.8 ± 19.0 | 105.1 ± 5.7 |
| 1 Hour after Glucose load | 329.5 ± 34.9 | 255.4 ± 19.7 | 202.4 ± 15.7* |
| 2 Hours after Glucose load | 280.8 ± 41.9 | 167.3 ± 17.5 | 137.1 ± 5.9 |

*P < 0.05 compared with the control group

As is apparent from Table 2, Compound A improved the glucose tolerance in the diabetic SHR.

TEST EXAMPLE 2

Acute toxicities of Compound A in rats through oral administration or intravenous injection were as follows.

TABLE 3

| Acute Toxicity in Rats LD$_{50}$ (mg/kg) | | |
|---|---|---|
| Male | Female | |
| 2438 | 1994 | (p.o.) |
| 807 | 783 | (i.v.) |

| Reference Example | |
|---|---|
| Compound A | 20 mg |
| Lactose | 50 mg |
| Corn Starch | 25.5 mg |
| Hydroxypropyl Cellulose | 4 mg |
| Magnesium Stearate | 0.5 mg |
| Total | 100 mg per one tablet |

According to the above formulation, the tablet containing Compound A was prepared by usual pharmaceutical techniques.

While the invention has been described in detail and with reference to specific embodiments thereof, it will be apparent to one skilled in the art that various changes and modifications can be made therein without departing from the spirit and scope thereof.

What is claimed is:

1. A method for treating a patient in need of an antidiabetaic agent which comprises administering thereto an antidiabetically effective amount of the compound 6-(1-imidazolylmethyl)-5,6,7,8-tetrahydronaphthalene-2-carboxylic acid or a pharmaceutically acceptable salt thereof.

2. The method of claim 1 wherein said compound is 6-(1-imidazolylmethyl)-5,6,7,8-tetrahydronaphthalene-2-carboxylic acid, hydrochloride hemihydrate.

* * * * *